(12) United States Patent
Awad et al.

(10) Patent No.: US 12,194,191 B1
(45) Date of Patent: Jan. 14, 2025

(54) **NANOBANDAGE SOLUTION WITH *Faidherbia albida* NANOPARTICLES AND NATURAL AND SYNTHETIC POLYMERS**

(71) Applicant: KING SAUD UNIVERSITY, Riyadh (SA)

(72) Inventors: Manal Ahmed Awad, Riyadh (SA); Afrah Fahad Alkhuriji, Riyadh (SA); Khalid Mustafa Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/605,547

(22) Filed: Mar. 14, 2024

(51) Int. Cl.
  *A61L 26/00* (2006.01)
  *A61K 36/48* (2006.01)
  *A61P 17/02* (2006.01)

(52) U.S. Cl.
  CPC .......... *A61L 26/0057* (2013.01); *A61K 36/48* (2013.01); *A61L 26/0061* (2013.01); *A61L 26/0095* (2013.01); *A61P 17/02* (2018.01); *A61K 2236/15* (2013.01); *A61K 2236/51* (2013.01); *A61L 2400/12* (2013.01)

(58) Field of Classification Search
  CPC ............. A61L 26/0057; A61L 26/0061; A61L 26/0095; A61L 2400/12; A61K 36/48; A61K 2236/15; A61K 2236/51; A61P 17/02
  See application file for complete search history.

(56) References Cited

U.S. PATENT DOCUMENTS

2016/0367676 A1\* 12/2016 Burnam .................. A61P 43/00

OTHER PUBLICATIONS

Tanwar M, et al "Natural gums and their derivatives based hydrogels: in biomedical, environment, agriculture, and food industry" Crit. Rev. Biotechnol.,44(2),2024 (ePub Jan. 22, 2023), pp. 275-301; doi: 10.1080/07388551.2022.2157702. (Year: 2023).\*
Kumar, K.P.A. et al., Tree gum-based nanostructures and their biomedical applications, Micro and Nano Technologies: Micro- and Nanoengineered Gum-Based Biomaterials for Drug Delivery and Biomedical Applications: pp. 383-407 (2022).
Singh, B. et al., Acacia gum polysaccharide based hydrogel wound dressings: Synthesis, characterization, drug delivery and biomedical properties, Carbohydrate Polymers 165: pp. 294-303 (2017).
Tanwar, M., Natural gums and their derivatives based hydrogels: in biomedical, environment, agriculture, and food industry, Critical Reviews in Biotechnology, Jan. 22, 2023, Abstract only (2023).
Cardena-Perez, Y.C. et al., Preparation and Characterization of Scaffold Nanofibers by Electrospinning, Based on Chitosan and Fibroin from Silkworm (*Bombyx mori*), Ingeniera y Competitividad 19(1): pp. 139-151 (2017).
Badne, F. et al., Synthesis and Characterization of Chitosan-Saponin Nanoparticle for Application in Plasmid DNA Delivery, Journal of Nanomaterials 371529, 8 pages (2015).

\* cited by examiner

*Primary Examiner* — Aaron J Kosar
(74) *Attorney, Agent, or Firm* — Nath, Goldberg & Meyer; Joshua B. Goldberg

(57) ABSTRACT

A nanobandage solution having *Faidherbia albida* nanoparticles, olibanum gum, and polyvinyl alcohol and methods of making the nanobandage solution and topically applying the nanobandage to a subject in need thereof are provided.

15 Claims, 5 Drawing Sheets

NANOBANDAGE SOLUTION WITH *Faidherbia albida* NANOPARTICLES AND NATURAL AND SYNTHETIC POLYMERS

BACKGROUND

Field

The disclosure of the present patent application relates to a nanobandage solution having *Faidherbia albida* nanoparticles and a mixture of natural and synthetic polymers, to methods of making the nanobandage solution, and to methods of healing wounds by topically applying the nanobandage solution to a wound on a subject in need thereof.

Description of Related Art

Nanobiotechnology has led to significant changes due to its use in various scientific fields. Skin wounds require unique care and treatment due to the fact that the body skin is the primary protection barrier towards pathogens. Therefore, quick and appropriate treatment of the wound is very important. Using nanotechnology, unique wound dressings can be created for various kinds of wounds and the time, place, and rate of drug release may be controlled. In addition to providing controlled drug delivery, nanobandages can be used as a cover for the wound to prevent microorganisms entering the body and creating an infection.

Natural polymers such as starch, Arabic gum, olibanum gum, and chitosan are widely used in biomedicine due to their acceptable properties of biocompatible, antimicrobial, non-toxic, giant cell migration, fibroblast activation, and increased healing rate of ulcers.

The *Faidherbia albida* plant is used to treat disorders such as diarrhea, skin diseases, rheumatism, and asthma, and is useful as an anti-inflammatory, anti-hemorrhagic and ophthalmic agent.

Thus, a nanobandage solution having *Faidherbia albida* nanoparticles and a mixture of natural and synthetic polymers, solving the aforementioned problems is desired.

SUMMARY

The present subject matter relates to a nanobandage solution having *Faidherbia albida* nanoparticles and a mixture of natural and synthetic polymers include nanoparticles synthesized from at least one *Faidherbia albida* extract and composite polymers of olibanum gum and polyvinyl alcohol.

In a further embodiment, the present subject matter includes methods of making a nanobandage solution having *Faidherbia albida* nanoparticles and a mixture of natural and synthetic polymers. These methods can include obtaining at least one plant extract of *Faidherbia albida*, spraying the plant extract into boiling water under ultrasonic conditions to obtain a plant nanoparticle solution, mixing aqueous solutions of gum olibanum and polyvinyl alcohol (PVA) to obtain a polymer solution, and then mixing together the plant nanoparticle solution and the polymer solution in equal ratios to obtain a nanofiber containing solution including *Faidherbia albida* nanoparticles, natural polymers, and synthetic polymers.

In a further embodiment, the present subject matter includes methods of topically applying a nanobandage solution to a wound on a subject in need thereof.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
FIG. 1 is a graph showing dynamic light scattering (DLS) results of the nanobandage.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

As used herein, "*Faidherbia albida*" refers to a species of leguminous plant that is native to Africa and the Middle East and is commonly referred to as apple-ring acacia, winter thorn, or the ana tree. *Faidherbia albida* is a thorny tree growing up to 6-30 m tall and up to 2 m in trunk diameter.

As used herein, "gum olibanum" or "olibanum gum" refers to an aromatic resin commonly used in incense and perfumes and often referred to as Frankincense. The resin is generally obtained by tapping Boswellia trees.

The nanobandage solution having *Faidherbia albida* nanoparticles and a mixture of natural and synthetic polymers include nanoparticles synthesized from at least one *Faidherbia albida* extract and composite polymers of olibanum gum and polyvinyl alcohol.

In an embodiment, the ratio of olibanum gum:polyvinyl alcohol in the nanobandage solution may be between about 1:1 and about 1:0.5 by weight.

In an embodiment, the concentration of olibanum gum in the nanobandage solution may be between about 1% and about 3% by weight.

In an embodiment, the concentration of polyvinyl alcohol in the nanobandage solution may be between about 1% and about 3% by weight.

In an embodiment, the concentration of *Faidherbia albida* nanoparticles is about 2 mg/ml to about 10 mg/ml, or about 5 mg/ml.

In a further embodiment, the present subject matter includes methods of making a nanobandage solution having *Faidherbia albida* nanoparticles and a mixture of natural and synthetic polymers. These methods can include obtaining at least one plant extract of *Faidherbia albida*, spraying the plant extract into boiling water under ultrasonic conditions to obtain a plant nanoparticle solution., mixing aqueous solutions of gum olibanum and polyvinyl alcohol (PVA) to obtain a polymer solution, and then mixing together the plant nanoparticle solution and the polymer solution in equal ratios to obtain a nanofiber containing solution including *Faidherbia albida* nanoparticles, natural polymers, and synthetic polymers.

In an embodiment, the *Faidherbia albida* nanoparticles may be obtained in powder form.

In an embodiment, the *Faidherbia albida* extract may be obtained by providing *Faidherbia albida* fruit, drying and powdering the *Faidherbia albida* fruit to obtain *Faidherbia albida* powder; suspending the *Faidherbia albida* powder in methanol, spraying the resulting aqueous solution of *Faidherbia albida* into boiling water dropwise under ultrasonic conditions, stirring the sonicated solution, and then freeze drying the solution to obtain *Faidherbia albida* nanoparticles in powder form.

In an embodiment, the *Faidherbia albida* extract may be obtained by providing *Faidherbia albida* fruit, washing and cleaning the *Faidherbia albida* fruit, and drying and powdering the *Faidherbia albida* fruit using a high-speed mechanical blender to obtain *Faidherbia albida* powder.

In an embodiment, about 50 mg of the *Faidherbia albida* powder may be suspended in 20 ml methanol while stirring.

In an embodiment, the resulting aqueous solution of *Faidherbia albida* is sprayed into about 50 ml boiling water dropwise with a flow rate of 0.2 ml/min over 5 minutes under ultrasonic conditions, and sonication is continued for about one hour.

In an embodiment, the sonicated solution is stirred at about 200 to about 800 rpm at room temperature for about 20 minutes and then freeze dried to obtain *Faidherbia albida* nanoparticles in powder form.

In a further embodiment, the present subject matter includes methods of topically applying a nanobandage solution to a wound on a subject in need thereof. The nanobandage solution may be formulated for direct topical application to a wound, in the form of a liquid or a gel. Alternatively, the nanobandage solution may first be applied to any known wound covering, including but not limited to a bandage, hydrogel, wrap, or the like, prior to application of the wound covering to the wound.

Preparation of the nanobandage solution in the form of a liquid, gel, hydrogel, or the like may be performed according to methods generally known in the art, and using such excipients, fillers, and gelling or thickening agents as are generally known in the art.

Topical administration of the nanobandage solution may result in increased wound healing and may be effective at preventing infection, especially when administered in combination with a wound covering.

The nanobandage solution having *Faidherbia albida* nanoparticles and a mixture of natural and synthetic polymers may be further understood in view of the following examples.

EXAMPLES

Example 1

Preparation of *Faidherbia albida* Nanoparticles

Fruits of *Faidherbia albida* were washed thoroughly under running tap water to remove any dirt or contaminants and any stems or inedible parts were removed. The fruits were then sliced or diced into smaller pieces and allowed to dry at room temperature. The dried fruits were powdered in a high-speed mechanical blender and kept in dried glass container and stored till used.

50 mg of *Faidherbia albida* prepared powder was taken in (20 ml) of methanol under stirrer. The resulting solution was sprayed into boiling water (50 mL) dropwise with a flow rate of 0.2 mL/min in 5 min under ultrasonic conditions, with an ultrasonic power of 100 W and a frequency of 20-30 kHz. After sonication for 1 hour, the contents were stirred at 200-800 rpm at room temperature for about 20 min. The resulting solution was then dried (by freezing drying) to obtain *Faidherbia albida* nanoparticles in powder form.

Example 2

Preparation of a Nanofiber Solution

First, a gum olibanum solution was prepared by providing gum olibanum, powdering the gum olibanum in a high-speed mechanical blender to obtain a smooth powder. Then, gum olibanum solution was prepared in boiling distilled water by adding 1-3 g of the smooth powder to 100-300 ml distilled water and soaking overnight at room temperature. Thereafter, the resulting solution was stirred at 800 rpm for 1 hour at room temperature. The resultant mixture was centrifuged at 2500 rpm for 10 min to remove insoluble materials.

Second, a solution of polyvinyl alcohol (PVA) was prepared by providing a 1-3 wt % polyvinyl alcohol (PVA) aqueous solution and stirring the PVA solution for a period of 5 h at (500-800 rpm) at 90° C. until the formation of clear solution.

Then, the gum olibanum solution and the PVA solution were mixed together in 1:1 or 1-0.5 ratio. The resultant mixture was stirred at low speed (200 rpm) for 3 h to ensure adequate mixing.

Finally, a nanobandage solution was prepared by gradually adding 5 mg/ml of synthesized *Faidherbia albida* nanoparticles in powder form into the mixture solution of gum olibanum and PVA under constant magnetic stirrer at room temperature. The obtained nanobandage solution was continuously stirred at 500 rpm for 10 min. Deaeration of the nanobandage solution was carried out using an ultrasound device.

Example 3

Characterizing the Nanofiber Solution

The mean particle diameter and polydispersity index (PdI) of nanocomposites was determined by dynamic light scattering (DLS) as shown in FIG. 1 and Table 1.

TABLE 1

DLS Results of the Nanobandage Solution

|  |  |  | Size (d · nm) | % Intensity | St Dev (d · nm) |
|---|---|---|---|---|---|
| Z-Average (d · nm): | 95.41 | Peak 1: | 178.4 | 84.4 | 88.12 |
| PdI: | 0.557 | Peak 2: | 29.65 | 7.2 | 8.842 |
| Intercept: | 0.929 | Peak 3: | 9.708 | 6.9 | 2.828 |
| Result Quality: | Refer to quality report |  |  |  |  |

Figure 2:
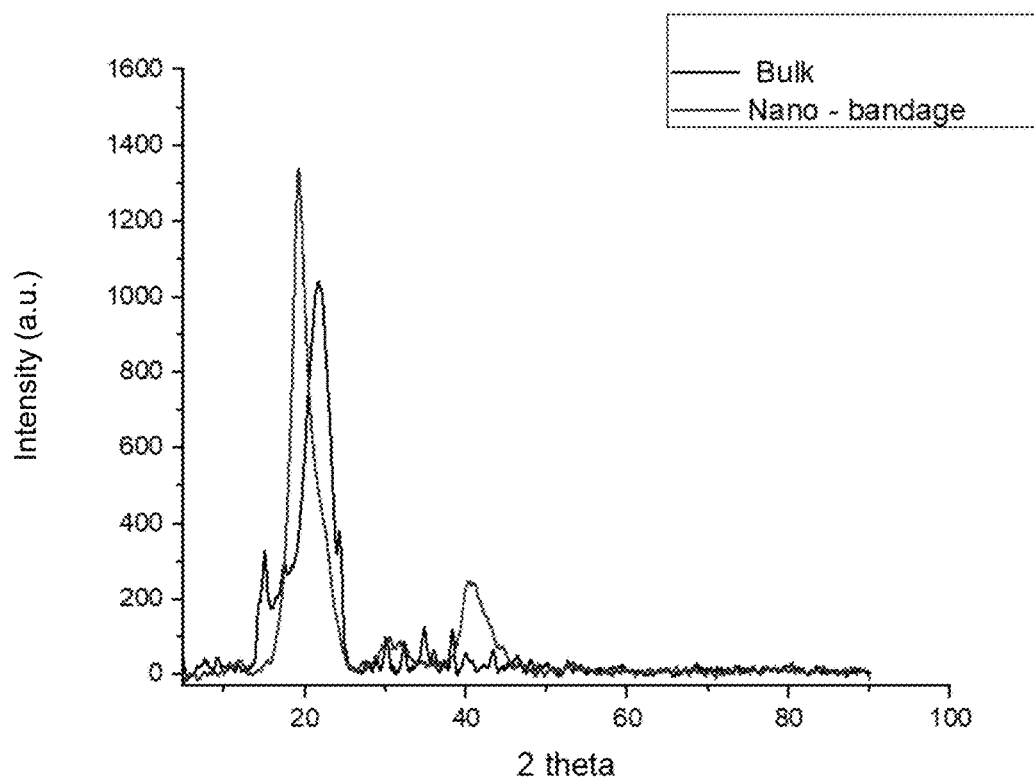
FIG. 2 is a graph showing x-ray diffraction (XRD) spectra of the nanobandage and *Faidherbia albida* extract.
Figure 3A:
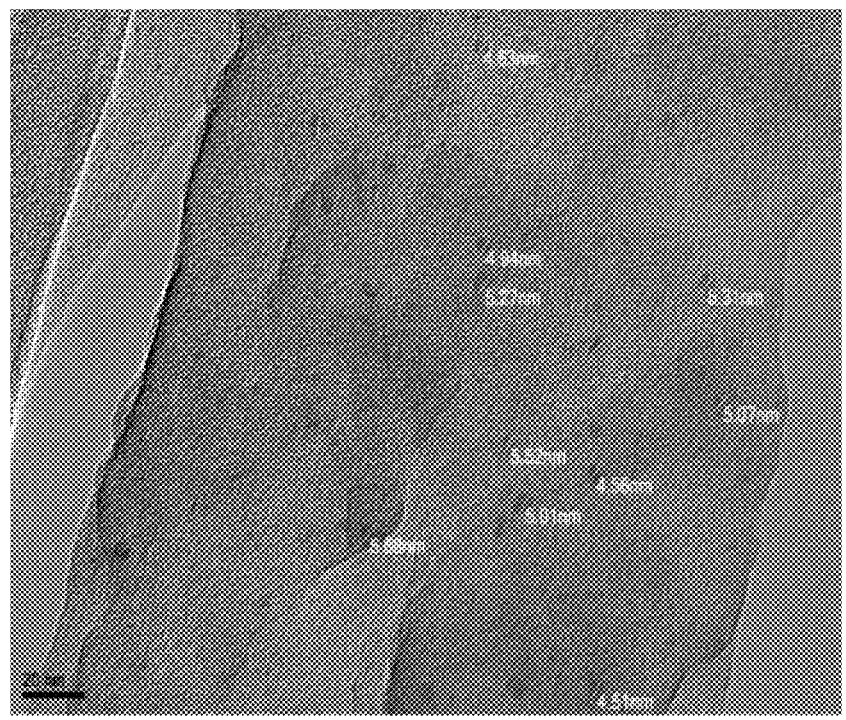
FIG. 3A is a transmission electron micrograph (TEM image) of the synthesized nanobandage.
Figure 3B:
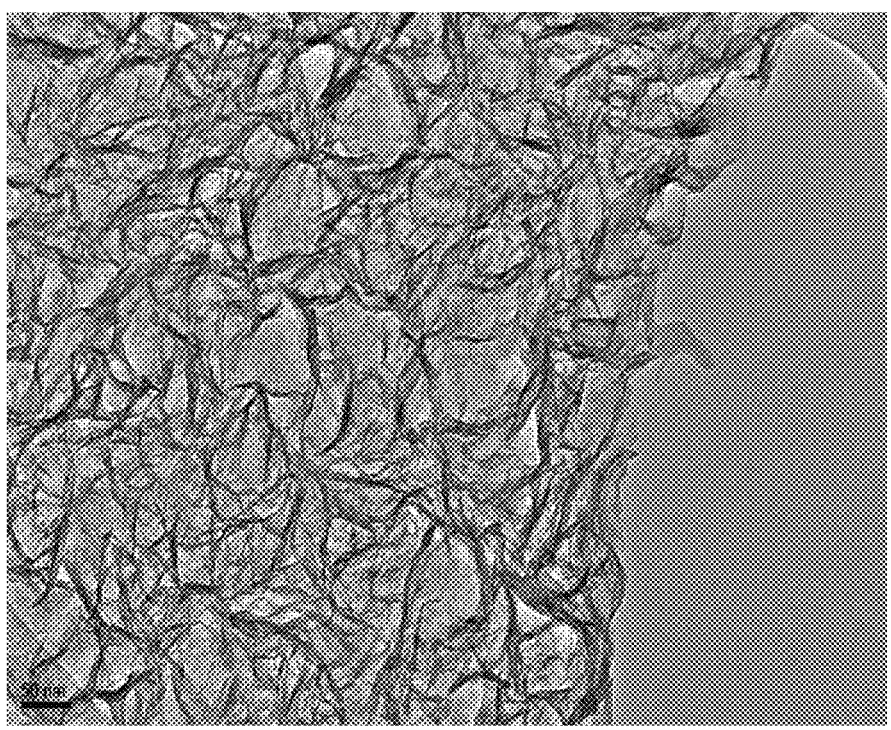
FIG. 3B is a transmission electron micrograph (TEM image) of the synthesized nanobandage.
Figure 3C:
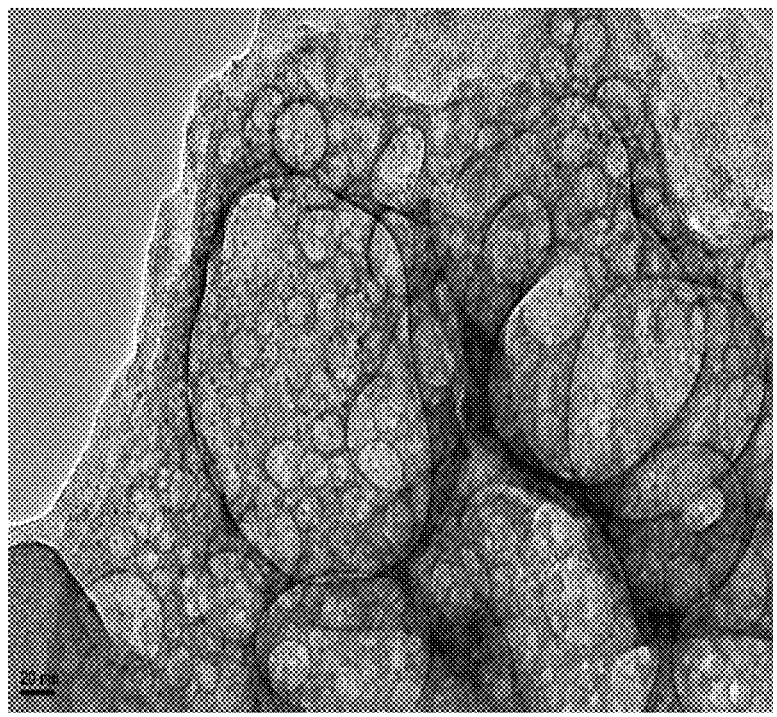
FIG. 3C is a transmission electron micrograph (TEM image) of the synthesized nanobandage.
Figure 3D:
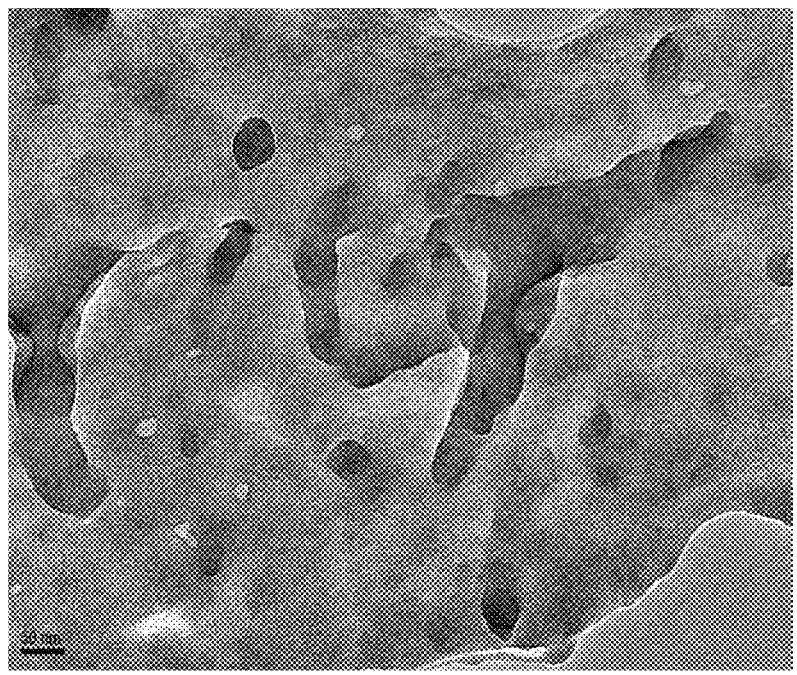
FIG. 3D is a transmission electron micrograph (TEM image) of the synthesized nanobandage.

X-ray diffraction (XRD) analysis was performed to determine the crystal structure of the nanobandage as well as to investigate the presence of synthesized nanoparticles (FIG. 2).

The shape and diameter of the prepared nanoparticles embedded into nanocomposite were obtained using Transmission electron microscopy (TEM) and the presence of synthesized nanoparticles in the nanofibers was confirmed (FIGS. 3A-3D).

Figure 4:
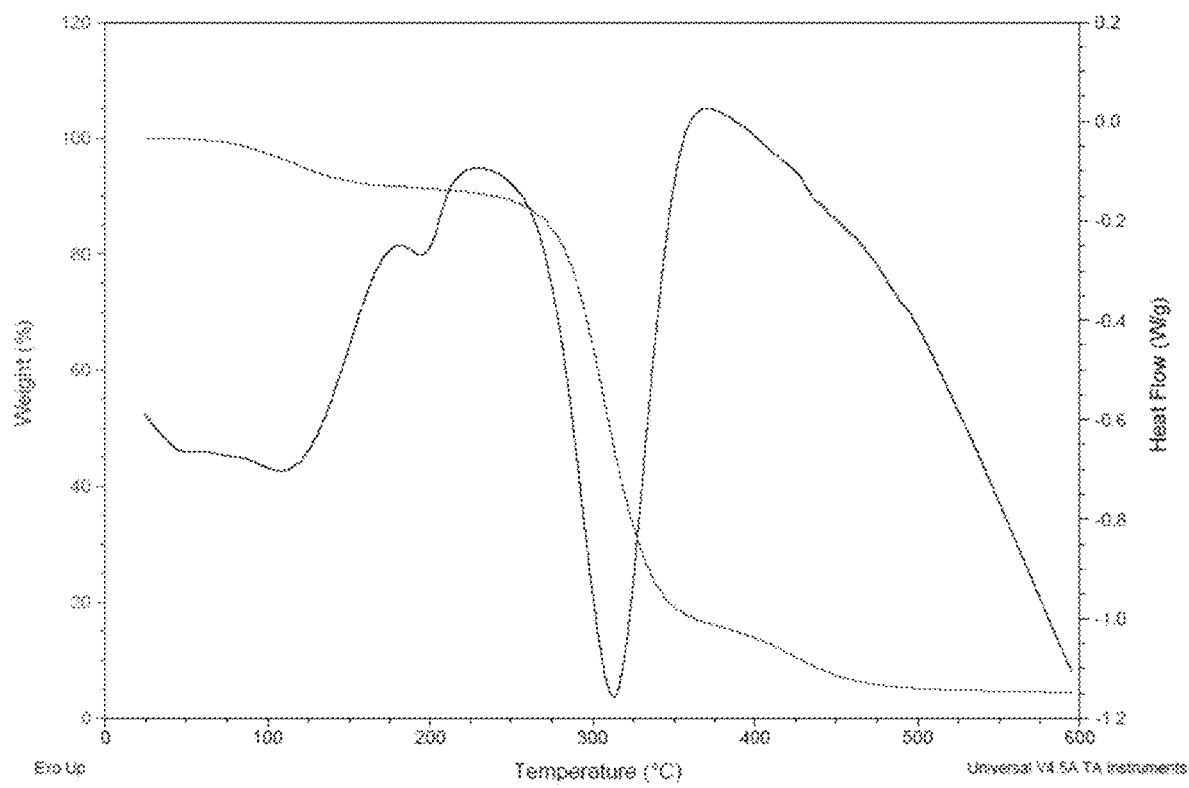
FIG. 4 is a graph showing the thermal gravimetric analysis (TGA) and differential scanning calorimetry (DSC) analysis of the synthesized nanobandage.

In a thermal study, both differential scanning calorimetry (DSC) and thermal gravimetric analysis (TGA) analyses confirmed that synthesized nanocomposite is thermostable (FIG. 4).

Figure 5:
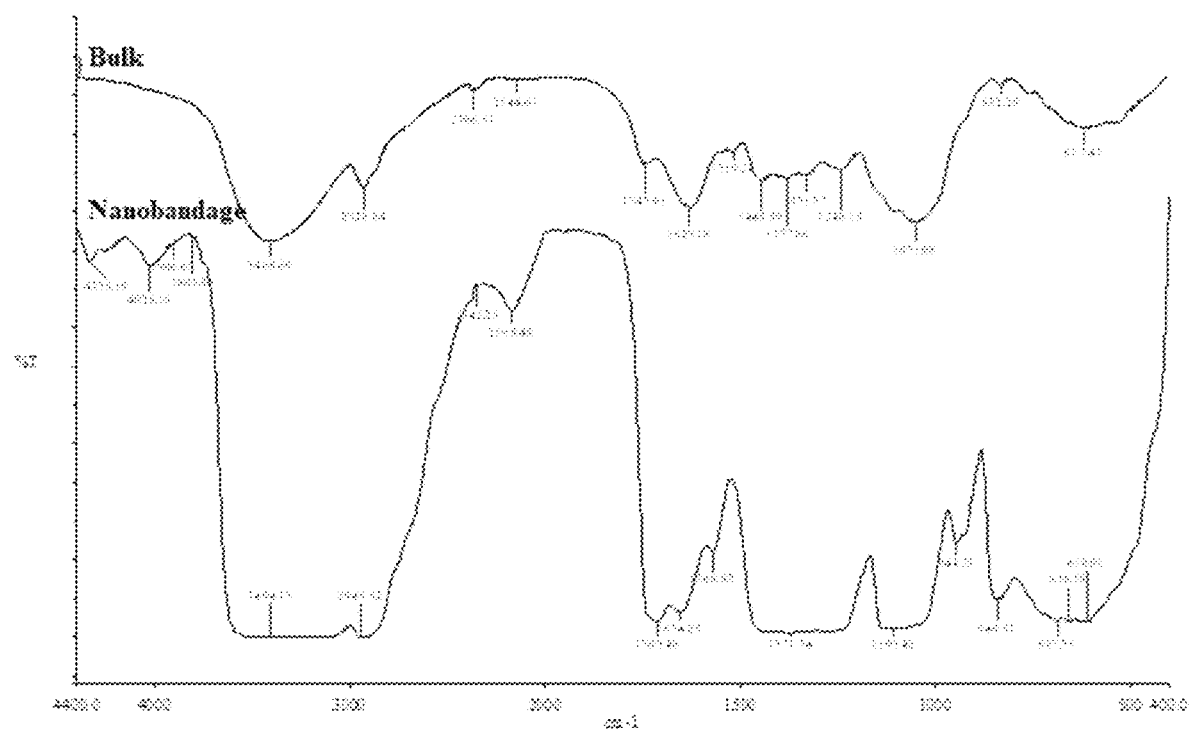
FIG. 5 is a graph showing fourier-transform infrared (FTIR) spectra of the synthesized nanobandage and the *Faidherbia albida* extract.

Fourier transforms infrared (FTIR) spectra of nanobandage solution are depicted in FIG. 5. Numerous functional groups were identified in the nanobandage and nanoparticles.

Example 4

Wound Healing Effect of the Nanobandage Solution

The present experimental study was conducted on adult male Wistar albino rats weighing 140-200 g. The animals were obtained from the Animal House of King Saud University, Faculty of Science (Riyadh, Saudi Arabia). The male rats were housed in metal cages with wire-grid floors. The animals were kept at standard housing facilities (25±2° C., 45±5% humidity and 12 hrs. light and dark cycles). They were fed on a standard laboratory chow and water ad libitum. All animals received humane care in compliance with the state authorities following the Saudi Arabia rules of animal protection.

Rats were randomly divided into four groups with 2 animals in each group and their hair was shaved in the dorsal area a 1.5 cm long by 2 cm wide (1.5l*2w) wound was given to each Rat. Then the animals were treated as follows:

Group 1 (Control): rats stayed without any treatment and the wound stayed without any covering for 17 days. The wound diameter was recorded every four days.

Group 2 (Saline Control): rats were treated with saline as another control, the saline was placed in pure cotton, the wet cotton was tied to the wound site with a bandage, and the cotton was replaced with the saline for a period of 17 days. The wound diameter was recorded every four days.

Group 3 (Crude *Faidherbia albida* fruit extract): Rats were treated with a crude *Faidherbia albida* fruit extract dissolved in normal saline. The solution was placed in pure cotton, the wet cotton was tied to the wound site with a bandage, and the cotton was replaced with the solution for a period of 17 days. The wound diameter was recorded every four days.

Group 4 (nanobandage solution): Rats were treated with the nanobandage solution prepared according to Examples 1-2, the nanobandage solution was dissolved in normal saline, placed in pure cotton, and the wet cotton was tied to the wound site with a bandage, and the cotton was replaced with the solution for a period of 17 days. The wound diameter was recorded every four days.

The results of this experiment are presented in Table 2. The evaluation of wound healing rate on day 10 after incision revealed that the wounds dressed with the synthesized nanobandage solution showed considerable signs of dermal healing and significantly healed faster compared with the treated control groups (normal saline and *F. albida* bulk).

TABLE 1

Wound Healing Results

| Day | Group 1 Control | Group 2 Saline Control | Group 3 Plant Extract | Group 4 Nanobandage Solution |
|---|---|---|---|---|
| 1 | 2.5 l * 1.5 w | 2 l * 1.5 w | 2 l * 1.5 w | 2 l * 1.5 w |
| 5 | 1.3 l * 1.1 w | 1.4 l * 1.3 w | 1.3 l * 1.2 w | 1.5 l * 1.4 w |
| 10 | 0.9 l * 0.9 w | 1 l * 1 w | 0.7 l * 0.4 w | 0.3 l * 0.9 w |
| 14 | 0.2 l * 0.6 w | 0.2 l * 0.3 w | 0.2 l * 0.w3 | 0.1 l * 0.3 w |
| 16 | 0.1 l * 0.2 w | 0.2 l * 0.2 w | 0 | 0 |
| 17 | 0 | 0 | 0 | 0 |

It is to be understood that the nanobandage solution having *Faidherbia albida* nanoparticles and a mixture of natural and synthetic polymers is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A nanobandage solution comprising:
   *Faidherbia albida* nanoparticles; and
   a composite of polyvinyl alcohol and gum olibanum.

2. The nanobandage solution of claim 1, wherein the ratio of gum olibanum:polyvinyl alcohol is between about 1:1 and 1:0.5.

3. The nanobandage solution of claim 2, wherein the ratio of gum olibanum:polyvinyl alcohol is about 1:1.

4. The nanobandage solution of claim 1, wherein the concentration of gum olibanum is between about 1% by weight and about 3% by weight.

5. The nanobandage solution of claim 1, wherein the concentration of polyvinyl alcohol is between about 1% by weight and about 3% by weight.

6. The nanobandage solution of claim 1, comprising about 5 mg/ml *Faidherbia albida* nanoparticles.

7. A method of making the nanobandage solution of claim 1, comprising:
   obtaining at least one plant extract of *Faidherbia albida*;
   spraying the at least one plant extract into boiling water under ultrasonic conditions to obtain a plant nanoparticle solution;
   mixing aqueous solutions of gum olibanum and polyvinyl alcohol (PVA) to obtain a polymer solution;
   mixing the plant nanoparticle solution and the polymer solution in equal ratios to obtain the nanobandage solution.

8. The method of claim 7, further comprising:
   providing *Faidherbia albida* fruit;
   drying and powdering the *Faidherbia albida* fruit to obtain *Faidherbia albida* powder;
   suspending the *Faidherbia albida* powder in methanol;
   spraying the resulting aqueous solution of *Faidherbia albida* into boiling water dropwise under ultrasonic conditions;
   stirring the sonicated solution, and then freeze drying the solution to obtain *Faidherbia albida* nanoparticles in powder form; and
   suspending the *Faidherbia albida* nanoparticles in methanol to obtain the at least one plant extract of *Faidherbia albida*.

9. The method of claim 8, comprising suspending about 50 mg of the *Faidherbia albida* powder in about 20 ml methanol.

10. The method of claim 7, wherein the spraying comprises spraying the at least one plant extract into about 50 ml boiling water dropwise with a flow rate of 0.2 ml/min over 5 minutes.

11. The method of claim 10, wherein the ultrasonic conditions comprise continuing sonication for about one hour.

12. The method of claim 7, comprising stirring the sonicated solution at about 200 to about 800 rpm at room temperature for about 20 minutes.

13. A method of improving wound healing in a subject in need thereof comprising administering the nanobandage solution of claim 1 topically to a wounded region of the subject's skin.

14. The method of claim 13, wherein the nanobandage solution is formulated as a liquid, gel, or hydrogel.

15. The method of claim 13 comprising administering the nanobandage solution to a wound covering and applying the wound covering to the wounded region of the subject's skin.

* * * * *